United States Patent
Rozsa et al.

(10) Patent No.: US 6,906,059 B2
(45) Date of Patent: Jun. 14, 2005

(54) PHARMACEUTICAL COMPOSITION WITH PROTECTIVE ACTION AGAINST OXIDATIVE/TOXIC SUBSTANCES, ESPECIALLY CARDIOTOXIC SUBSTANCES

(75) Inventors: Zsuzsanna Rozsa, deceased, late of Szeged (HU); by Zsuzsanna Lonovics, legal representative, Taszar (HU); Julius Gy. Papp, Szeged (HU); Dirk Thormaehlen, Rheden (DE); Harald Waldeck, Isernhagen (DE)

(73) Assignee: Solvay Pharmaceuticals, Hannover (DE)

( * ) Notice: Subject to any disclaimer, the term of this patent is extended or adjusted under 35 U.S.C. 154(b) by 13 days.

(21) Appl. No.: 10/043,268

(22) Filed: Jan. 14, 2002

(65) Prior Publication Data

US 2003/0040512 A1 Feb. 27, 2003

Related U.S. Application Data

(63) Continuation of application No. PCT/EP00/06525, filed on Jul. 10, 2000.

(30) Foreign Application Priority Data

Jul. 13, 1999 (DE) .......................... 199 32 555

(51) Int. Cl.$^7$ .......................... A61K 31/55; A61K 31/12
(52) U.S. Cl. ............... 514/212.07; 514/34; 514/217.11; 514/217.12; 514/676; 514/680; 514/685
(58) Field of Search .............................. 514/34, 212.07, 514/217.11, 217.12, 676, 680, 685

(56) References Cited

U.S. PATENT DOCUMENTS

| | | | | |
|---|---|---|---|---|
| 5,677,297 A | | 10/1997 | Waldeck et al. | ............ 514/211 |
| 5,783,573 A | * | 7/1998 | Rozsa et al. | ........... 514/212.07 |
| 6,482,820 B2 | * | 11/2002 | Wilkins et al. | ........ 514/212.07 |

FOREIGN PATENT DOCUMENTS

WO    WO 01/03699    *   1/2001

OTHER PUBLICATIONS

International Search Report, (Dec. 15, 2000).

* cited by examiner

Primary Examiner—Porfirio Nazario-Gonzalez
(74) Attorney, Agent, or Firm—Crowell & Moring LLP

(57) ABSTRACT

The use of benzazepin-N-acetic acid derivatives which contain an oxo group in the a position to the nitrogen atom and are substituted in the 3 position by a 1-(carboxyalkyl)-cyclopentyl-carbonyl-amino radical, and of their salts and biolabile esters, for the prophylaxis and/or treatment of heart damage caused by cardiotoxic doses of medicaments or chemicals, in larger mammals and in particular humans. The invention is particularly applicable to the prophylaxis and/or treatment of heart damage, in particular to the myocardium, which may occur during cytostatic chemotherapy. The invention also includes the use of the afore-mentioned benzazepin-N-acetic acid derivatives for adjuvant treatment in therapies in which medicaments having oxidative-toxic side-effects are used, and the preparation of medicaments suitable for this prophylaxis and/or treatment or adjuvant treatment.

34 Claims, No Drawings

PHARMACEUTICAL COMPOSITION WITH PROTECTIVE ACTION AGAINST OXIDATIVE/TOXIC SUBSTANCES, ESPECIALLY CARDIOTOXIC SUBSTANCES

CROSS REFERENCE TO RELATED APPLICATIONS

This application is a continuation of international patent application no. PCT/EP00/06525, filed Jul. 10, 2000, designating the United States of America, the entire disclosure of which is incorporated herein by reference. Priority is claimed base on Federal Republic of Germany patent application no. DE 199 32 555.3, filed Jul. 13, 1999.

BACKGROUND OF THE INVENTION

The present invention relates to the use of benzazepin-N-acetic acid derivatives which contain an oxo group in the a position to the nitrogen atom and are substituted in the 3 position by a 1-(carboxyalkyl)-cyclopentyl-carbonyl-amino radical, and of their salts and biolabile esters, in particular for the prophylaxis and/or treatment of damage to the heart in larger mammals and in particular humans which is caused by oxidative-toxic, in particular cardiotoxic, doses of medicaments or chemicals, and to the preparation of medicaments suitable for this prophylaxis and/or treatment. Generally, the invention also relates to the use of the afore-mentioned benzazepin-N-acetic acid derivatives for adjuvant treatment in therapies in which medicaments having oxidative-toxic, and in particular cardiotoxic, side-effects are used. Preferably, the invention relates to the prophylaxis and treatment of damage to the heart, in particular to the myocardium, which may occur during cytostatic chemotherapy.

It is known that the cytostatic agents used in the chemotherapy of malignant tumours may have cardiotoxic properties as an unwanted side-effect. Thus, some antibiotics are also used in cytostatic therapy which, owing to their generally toxic properties, cannot be used for the treatment of bacterial infections. These include, for example, the anthracyclines isolated from streptomyces species, which are among the important more recent developments in the field of cytostatic agents. However, the clinical usability of the anthracyclines is limited by their more or less greatly marked cardiotoxicity. The cardiotoxicity in this case is correlated to the total dose administered, and is frequently irreversible. Presumably, the heart damage and the cytostatic effects of these antibiotics are based at least in part on the membrane action thereof, by means of which the membrane fluidity and permeability is increased by the binding of the antibiotic to components of the cell membrane. Furthermore, oxidative damage may also be considered as an additional cause.

Typical antibiotics used in cytostatic therapy include the anthracyclines daunorubicin and the prodrug thereof, zorubicin, doxorubicin (adriamycin) and epirubicin, and the synthetic antibiotic mitoxantrone.

Benzazepin-N-acetic acid derivatives which contain an oxo group in the a position to the nitrogen atom and are substituted in the 3 position by a 1-(carboxyalkyl)-cyclopentyl-carbonyl-amino radical, and their salts and biolabile esters fall within the scope of protection of benzazepin-, benzoxazepin- and benzothiazepin-N-acetic acid derivatives described in Waldeck et al., U.S. Pat. No. 5,677,297 (=DE 195 10 566), which contain an oxo group in the a position to the nitrogen atom and are substituted in the 3 position by a 1-(carboxyalkyl)-cyclopentyl-carbonyl-amino radical, and which have NEP-inhibiting effects on the heart. The benzazepin-N-acetic acid compounds used within the scope of the present invention may be prepared using the process described in Waldeck et al., U.S. Pat. No. 5,677,297, the entire disclosure of which is incorporated herein by reference.

SUMMARY OF THE INVENTION

It is the object of the invention to provide new and improved methods and pharmaceutical preparations for the prophylaxis and/or treatment of damage to the heart which occurs in connection with the use of cardiotoxic doses of medicaments or chemicals.

According to the invention, compounds of the general formula I

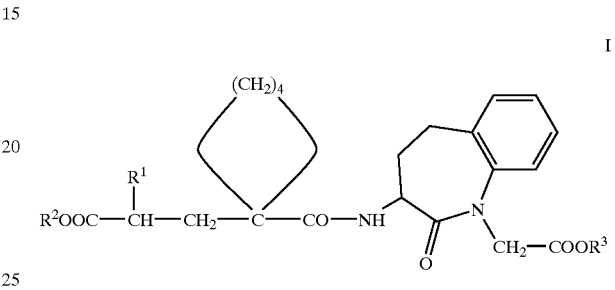

in which
$R^1$ is a phenyl lower-alkyl group which may optionally be substituted in the phenyl ring by lower alkyl, lower alkoxy or halogen, or for a naphthyl lower-alkyl group,
$R^2$ is hydrogen or a group forming a biolabile ester,
$R^3$ is hydrogen or a group forming a biolabile ester,
and physiologically compatible salts of the acids of Formula I are used for the preparation of pharmaceutical preparations for the prophylaxis and/or treatment of damage to the heart, in particular to the myocardium, induced by cardiotoxic doses of medicaments, in particular of cytostatic agents, preferably of cytostatic antibiotics, or chemicals, in larger mammals and humans.

Furthermore, the compounds of the above general formula I and of physiologically compatible salts of acids of Formula I are used for the preparation of pharmaceutical preparations for adjuvant treatment in larger mammals and humans in therapies in which medicaments having oxidative-cytotoxic, in particular oxidative-cardiotoxic, side-effects, are used.

In accordance with one aspect of the invention a method is provided for inhibiting or treating heart damage induced by a cardiotoxic medicament in a mammal, the method comprising administering to said mammal an effective cardioprotective amount of a compound corresponding to Formula I

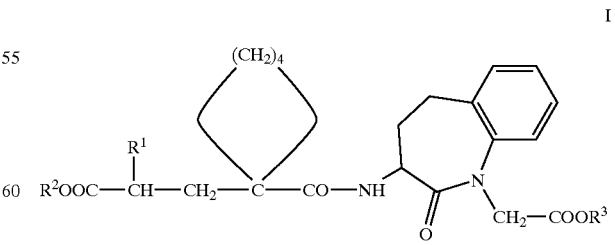

wherein
$R^1$ is a phenyl lower-alkyl group which may optionally be substituted in the phenyl ring by lower alkyl, lower alkoxy or halogen, or for a naphthyl lower-alkyl group, $R^2$ is hydrogen or a group forming a biolabile ester, and
$R^3$ is hydrogen or a group forming a biolabile ester, or a physiologically compatible salt thereof.

In accordance with another aspect of the invention, treatment methods involving therapeutic administration to a mammal of a substance having oxidative-cytotoxic side effects, are improved by administering to said mammal an effective oxidative-cytotoxic side effect inhibiting amount of a compound corresponding to Formula I

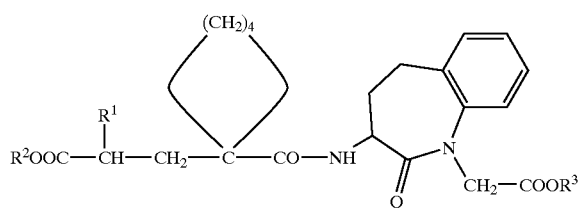

wherein $R^1$ is a phenyl lower-alkyl group which may optionally be substituted in the phenyl ring by lower alkyl, lower alkoxy or halogen, or for a naphthyl lower-alkyl group,
$R^2$ is hydrogen or a group forming a biolabile ester, and
$R^3$ is hydrogen or a group forming a biolabile ester, or a physiologically compatible salt thereof.

In accordance with a further aspect of the invention, a pharmaceutical composition is provided comprising in combination a medicament having cardiotoxic, oxidative-cytotoxic or oxidative-cardiotoxic side-effects, and a compound corresponding to Formula I

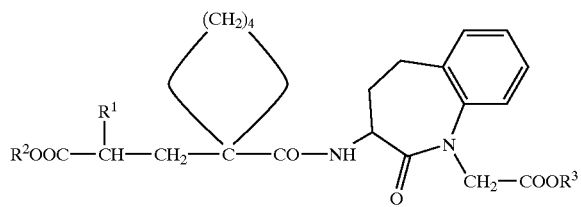

wherein $R^1$ is a phenyl lower-alkyl group which may optionally be substituted in the phenyl ring by lower alkyl, lower alkoxy or halogen, or for a naphthyl lower-alkyl group,
$R^2$ is hydrogen or a group forming a biolabile ester, and
$R^3$ is hydrogen or a group forming a biolabile ester, or a physiologically compatible salt thereof.

In yet another aspect of the invention, a pharmaceutical package is provided comprising at least one dosage unit of a medicament having cardiotoxic, oxidative-cytotoxic or oxidative-cardiotoxic side-effects, and at least one dosage unit of a compound corresponding to Formula I

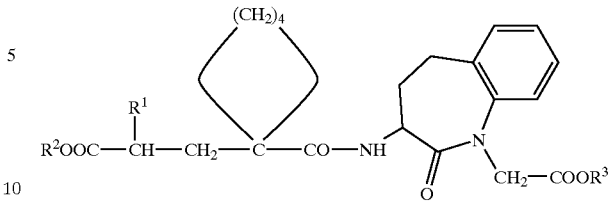

wherein
$R^1$ is a phenyl lower-alkyl group which may optionally be substituted in the phenyl ring by lower alkyl, lower alkoxy or halogen, or for a naphthyl lower-alkyl group,
$R^2$ is hydrogen or a group forming a biolabile ester, and
$R^3$ is hydrogen or a group forming a biolabile ester,
or a physiologically compatible salt thereof.

Where the substituents in the compounds of Formula I are or contain lower alkyl or alkoxy groups, these may be straight-chain or branched and contain, in particular, 1 to 4, preferably 1 to 2, carbon atoms and are preferably methyl or methoxy. Where the substituents contain halogen, fluorine, chlorine or bromine is preferred, and fluorine or chlorine is particularly suitable.

In the radical $R^1$, the lower alkylene chain may contain 1 to 4, preferably 1 to 2, carbon atoms. In particular, $R^1$ is an optionally substituted phenethyl group which can optionally be substituted one or more times by halogen, lower alkoxy or lower alkyl, or is a naphthylethyl group.

The compounds of Formula I are optionally esterified dicarboxylic acid derivatives. Depending on the form of administration, biolabile monoesters, particularly compounds in which $R^2$ is a group forming a biolabile ester and $R^3$ is hydrogen, or dicarboxylic acids are preferred, the latter being particularly suitable for intravenous (i.v.) administration.

Suitable groups forming biolabile esters $R^2$ and $R^3$ include lower alkyl groups, phenyl or phenyl-lower-alkyl groups which are optionally substituted in the phenyl ring by lower alkyl or by a lower alkylene chain bonded to two adjacent carbon atoms, dioxolanylmethyl groups which are optionally substituted in the dioxolane ring by lower alkyl, or $C_2$–$C_6$-alkanoyloxymethyl groups optionally substituted on the oxymethyl group by lower alkyl. Where the group forming a biolabile ester $R^2$ or $R^3$ is lower alkyl, this may be a preferably unbranched alkyl group with 1 to 4, preferably 2, carbon atoms. Where the group forming a biolabile ester is an optionally substituted phenyl lower-alkyl group, its alkylene chain may contain 1 to 3, preferably 1, carbon atoms. Where the phenyl ring is substituted by a lower alkylene chain, this may contain 3 to 4, particularly 3, carbon atoms. Phenyl, benzyl or indanyl are particularly suitable as phenyl-containing sub-stituents $R^2$ and/or $R^3$. Where $R^2$ and/o $R^3$ are an optionally substituted alkanoyloxymethyl group, their alkanoyloxy group may contain 2 to 6, preferably 3 to 5, carbon atoms and is preferably branched and can be, for example, a pivaloyloxymethyl radical (=tert.-butylcarbonyloxymethyl radical).

Suitable physiologically compatible salts of dicarboxylic acids or monoesters of Formula I include their alkali metal, alkaline earth metal or ammonium salts, for example sodium or calcium salts or salts with physiologically compatible, pharmacologically neutral organic amines such as, for example, diethylamine or tert.-butylamine.

The compounds of Formula I contain two chiral carbon atoms, namely the carbon atom which is in the 3 position of the ring framework and bears the amide side-chain, and the carbon atom of the amide side-chain which bears the radical $R^1$. The compounds can therefore exist in several optically active stereoisomeric forms or as a racemate. According to the present invention both the racemic mixtures and the isomerically pure compounds of Formula I may be used.

It has now surprisingly been found that the group of compounds of Formula I used according to the invention and their physiologically compatible salts of the acids, in addition to their previously-known NEP-inhibiting properties, also have the ability to counteract damage to the heart due to cardiotoxic substances (active substances, chemicals), in particular catabolic and anabolic processes (remodelling) such as those of myocardial hypertrophy and fibrous tissue growth, and thus exert a protective action against these cardiotoxic substances in the heart. The compounds of Formula I and their physiologically compatible salts of the acids thus have a preventive or damage-reducing and hence anti-cardiotoxic effect in relation to damage to the heart due to cardiotoxic substances, in humans and larger mammals. The compounds of Formula I, including their salts of acids and the biolabile esters thereof, are therefore suitable for the prophylaxis and/or treatment of damage to the heart, in particular to the myocardium, induced by cardiotoxic doses of medicaments or chemicals of widely-varying kinds. The substances causally responsible for damage to the heart, such as medicaments, may be of a diverse nature, e.g. the cytostatic agents used in the chemotherapy of malignant tumours, in particular cytostatic antibiotics. Furthermore, it was discovered in this connection that the group of compounds of Formula I used according to the invention very generally also exhibit antioxidative properties. These properties may result in advantageous cytoprotective and in particular cardioprotective effects, so that the compounds used according to the invention are suitable for adjuvant treatment in larger mammals and humans in therapies in which medicaments having oxidative-cytotoxic and in particular oxidative-cardiotoxic side-effects are used.

The anti-cardiotoxic action, i.e. the preventive or damage-reducing action directed against damage to the heart due to cardiotoxic substances, and the antioxidative effect of the compounds of Formula I used according to the invention was demonstrated in pharmacological tests in vivo on rabbits and rats each with adriamycin-induced cardiomyopathy. It was demonstrated by measuring the action of the substances on rabbits in relation to the inhibition or reduction of adriamycin-induced remodelling processes on the heart, and by measuring the antioxidant activity of the compounds on rats.

DESCRIPTION OF TEST METHODS

A) The tests were carried out on rabbits of both sexes having an initial body weight of 2.1±0.2 kg. The animals were divided into 3 groups:

1. untreated animals (=control animals, n=20);
2. animals treated with adriamycin (+placebo instead of test substance, n=8);
3. animals treated with adriamycin and test substance (n=8).

The test substance used was (3S,2R')-3-{1-[2'-(ethoxycarbonyl)-4'-phenyl-butyl]-cyclopentane-1-carbonylamino}-2,3,4,5-tetrahydro-2-oxo-1H-1-benzazepin-1-acetic acid, which is representative of the substances of Formula I usable according to the invention.

Groups 2 and 3 were administered 1 mg/kg adriamycin i.v. twice a week for 4 weeks. Group 3 of rabbits having adriamycin-induced cardiomyopathy was administered a daily oral dose of the test substance (30 mg/kg body weight) for 4 weeks, starting on the first day of adriamycin treatment, with their food. Once the 4 weeks had ended, the hearts were isolated and weighed. Then they were fixed with formalin for later biochemical investigations (hydroxyproline content of the heart tissue, measured with the HPLC amino acid analysis after Blankenship, D. T. et al., Aunal. Biochem. 178, 227–232, 1989 and Schuster, R., J. Chromatogr. 431, 271 –284, 1989). Both the increase in heart weight in relation to body weight and the hydroxyproline content in the heart tissue compared with normal values are indicators of remodelling processes taking place in the heart. The test results are compiled in the following Table I.

TABLE I

Reduction of the cardiac remodelling processes caused by adriamycin by the test substance in a rabbit's heart

| Measured parameters | Group 1: Untreated animals, n = 20 (X ± SEM) | Group 2: Animals treated with adriamycin + placebo, n = 8 (X ± SEM) | Group 3: Animals treated with adriamycin + test substance, n = 8 (X ± SEM) | % Effect of the test substance (group 3 v. 2) |
|---|---|---|---|---|
| Ratio of heart weights to body weight (g) | 2.01 ± 0.08 | 3.39 ± 0.13*** | 2.79 ± 0.08+ | −17.7 |
| Hydroxyproline content of the heart (μg/ng) | 6.66 ± 0.45 | 10.68 ± 0.69*** | 9.26 ± 2.51 | −13.3 |

SEM = Standard Error of the Mean
***p < 0.001 v. untreated (group 1)
+p < 0.01 v. adriamycin + placebo (group 2)

With this test method, the treatment with the test substance resulted in a statistically significant reduction in the heart/body weight ratio compared with the control animals treated with adriamycin. Adriamycin treatment (group 2) increased the heart/body weight ratio (measured in g/kg) highly statistically significantly by about 69%, compared with the untreated control group (group 1). If the test substance was administered in addition to adriamycin (group 3), the adriamycin-induced increase in the heart/body weight ratio was reduced statistically significantly by about 18% compared with the animals treated with placebos (group 2).

The left-ventricular myocardial hydroxyproline concentration, which is a measurement of cardiac fibrous tissue growth, was less in the animals treated with test substance (group 3) than in the control animals treated with adriamycin (group 2). Adriamycin treatment increased the and Bieri, J. G., Clin. Chem. 29, 708–712, 1983. The test results are compiled in the following Table II.

TABLE II

Inhibition of the pro-oxidative action of adriamycin by the test substance in rats

| Measured plasma parameters | Group 1: Untreated animals, n = 19 (X ± SEM) | Group 2: Animals treated with adriamycin + placebo, n = 14 (X ± SEM) | Group 3: Animals treated with test substance, n = 11 (X ± SEM) | Group 4: Animals treated with adriamycin + test substance, n = 14 (X ± SEM) | % Effect of the test substance Group 4 v. 2 | Group 3 v. 1 |
|---|---|---|---|---|---|---|
| α-Tocopherol (Vitamin E) (μg/dl) | 337.0 ± 21.0 | 338.2 ± 28.0 | 657.8 ± 21.0*** | 407.9 ± 33.0 | +20.6 | +95.2 |
| Lipid peroxides (measured as malonic dialdehyde thiobarbituric acid adducts) (μmol/l) | 1.939 ± 0.085 | 4.476 ± 0.404*** | 2.319 ± 0.086* | 3.030 ± 0.235+++ | −32.3 | +19.6 |
| Ferroxidase activity (IU/l) | 0.2698 ± 0.0107 | 0.3289 ± 0.317* | 0.2545 ± 0.0104 | 0.2534 ± 0.0128+ | −23.0 | −5.7 |

SEM = Standard Error of the Mean
*p < 0.05 v. untreated (group 1)
***p < 0.001 v. untreated (group 1)
+p < 0.05 v. adriamycin + placebo (group 2)
+++p < 0.001 v. adriamycin + placebo (group 2)

myocardial hydroxyproline content (measured in μg/ng) of the heart highly statistically significantly, by about 60%, compared with the untreated control group (group 1). If the test substance was also administered in addition to adriamycin (group 3), the adriamycin-induced increase in the hydroxyproline content could be reduced by about 13% compared with animals treated with placebo (group 2). It can be concluded from the results that the remodelling process of the extracellular myocardial matrix is significantly reduced by administering the test substance.

B) The tests were carried out on male Wistar rats having an initial body weight of 229 to 277 g. The animals were divided into 4 groups:
 1. untreated animals (=control animals, n=19);
 2. animals treated with adriamycin (+placebo instead of test substance, n=14);
 3. animals treated with test substance (n=11);
 4. animals treated with adriamycin and test substance (n=14).

The test substance used was (3S,2R')-3-{1-[2'-(ethoxycarbonyl)-4'-phenyl-butyl]-cyclopentane-1-carbonylamino}-2,3,4,5-tetrahydro-2-oxo-1H-1-benzazepin-1-acetic acid, being representative of the substances of Formula I usable according to the invention.

The animals of groups 2 and 4 were administered 15 mg/kg adriamycin intraperitoneally over a period of two weeks. The animals of group 4 were administered 30 mg/kg of the test substance daily for two weeks with their food, starting with the first day of adriamycin treatment. The animals of group 3 were likewise administered 30 mg/kg of the test substance daily for two weeks with their food (but without adriamycin).

Once the two-weeks' treatment had ended, the animals were anaesthetised with pentobarbital (50 mg/kg i.p.) and venous blood samples were taken, from which plasma was obtained. The concentration of lipid-peroxides and the ferroxidase activity in the plasma was measured using the methods of Wong, S. H. Y. et al., Clin. Chem. 33, 214–220, 1987 or Johnson, D. A. et al., Clin. Chem. 13, 142–150, 1967. Furthermore, the α-tocopherol concentration in the plasma was measured using the method of Catignani, G. L.

The test substance exhibited directly antioxidative effects (e.g. increase in plasma α-tocopherol compared with the control animals and the animals treated with adriamycin), and inhibited the pro-oxidative action of adriamycin, which was demonstrated by a significant reduction in lipid oxidation and plasma ferroxidase activity compared with the control rats treated with adriamycin. Administering the test substance increased the α-tocopherol content (Vitamin E, measured in μg/dl) in the plasma of the test animals in group 3 statistically highly significantly by about 95%, compared with the control animals (group 1). In the animals treated with adriamycin and test substance (group 4), a considerable increase in the α-tocopherol content in the plasma by about 21% was likewise noted, compared with the animals of group 2 (adriamycin+placebo). The concentration of lipid peroxides in the rat plasma (measured as malonic dialdehyde thiobarbituric acid adducts) increased statistically highly significantly, by about 131%, for the animals of group 2, who were treated with adriamycin, compared with the control group (group 1). If the test substance was administered in addition to adriamycin (group 4), the increase in the concentration of lipid peroxides in the plasma, induced by the adriamycin, was reduced statistically highly significantly by about 32% compared with group 2 (adriamycin+placebo). The total activity of the ferroxidase (measured in IU/l) in the rat plasma increased statistically significantly in the group treated with adriamycin (group 2) by about 22% compared with the control group (group 1). If the test substance was administered in addition to adriamycin (group 4), the ferroxidase activity decreased statistically significantly by 23% compared with group 2 (adriamycin+placebo), and thus corresponded approximately to the ferroxidase activity which was determined for the control group (group 1).

It can be concluded from these test results that the pro-oxidative action of adriamycin plays a part in the cardiotoxicity caused by this substance, and that the test substance has a positive influence on this cardiotoxicity due to its anti-oxidative properties.

In view of their effect described above, the compounds of Formula I are suitable as medicaments for larger mammals and in particular humans for the prophylaxis and/or treatment of damage in the heart caused by damaging influences of cardiotoxic doses of medicaments and other chemical substances, such as in particular remodelling processes on the heart, such as myocardial hypertrophy or fibrous tissue growth. The compounds of the general formula I also have an advantageous antioxidative effect. This means that damaging oxidative influences of other medicaments, such as cytostatic agents, can be reduced. The compounds of Formula I can thus be used as medicaments for adjuvant treatment in those therapies in which medicaments having oxidative-toxic and in particular cardiotoxic side-effects are administered. For this purpose, dicarboxylic acids of Formula I and their salts are advantageously used in pharmaceutical compositions for parenteral, particularly i.v., administration, and mono- or diesters of Formula I are expediently used in orally administered medicament forms. The doses to be used may differ between individuals and will naturally vary according to the nature of the condition to be treated, the substance used and the form of administration. For example, parenteral formulations will generally contain less active substance than oral preparations. Generally, however, pharmaceutical compositions having an active substance content of 1 to 200 mg per individual dose are suitable for administration to larger mammals, in particular humans.

As therapeutic agents, the compounds of Formula I may be contained with conventional pharmaceutical adjuvants in pharmaceutical preparations such as tablets, capsules, suppositories or solutions. These pharmaceutical preparations may be prepared according to known methods, using conventional solid or liquid vehicles such as lactose, starch or talc, or liquid paraffins and/or using conventional pharmaceutical adjuvants, such as tablet disintegrating agents, solubilizing agents or preservatives.

The invention also relates to products which contain a medicament having cardiotoxic side-effects or a medicament having oxidative-cytotoxic or oxidative-cardiotoxic side-effects, in particular a cytostatic agent having cardiotoxic side-effects, and a compound of the above Formula I or a physiologically compatible salt of acids of Formula I as a combination preparation for simultaneous, separate or stage-wise application in therapy with the medicament having cardiotoxic side-effects. In particular, these products contain as cytostatic agent a cytostatic antibiotic and a compound of Formula I or a physiologically compatible salt of acids of Formula I as a combination preparation for simultaneous, separate or stage-wise application in cytostatic chemotherapy. Such products may for example contain a cytostatic antibiotic from the group consisting of the anthracyclines, mitoxantrone or a prodrug thereof as antibiotic. In this case, the anthracycline may be in particular daunorubicin, doxorubicin (adriamycin) or epirubicin or a prodrug thereof, preferably doxorubicin (adriamycin) or a prodrug thereof.

The following examples are intended to illustrate the invention in further detail, without limiting its scope. Examples 1 and 2 below describe pharmaceutical preparations according to the invention which contain an active substance of Formula I, and the preparation of such pharmaceutical preparations. As noted above, the compounds of Formula I used according to the invention may be prepared for this purpose by the methods described in Waldeck et al., U.S. Pat. No. 5,677,297, which is incorporated herein by reference.

EXAMPLE 1

Tablets Containing (3S,2'R)-3-{1-[2'-(ethoxycarbonyl)-4'-phenyl-butyl]-cyclopentan-1-carbonylamino}-2,3,4,5-tetrahydro-2-oxo-1 H-1-benzazepin-1-acetic acid Tablets were prepared with the following composition per tablet:

| | |
|---|---:|
| (3S,2'R)-3-{1-[2'-(ethoxycarbonyl)-4'-phenyl-butyl]-cyclopentan-1-carbonylamino}-2,3,4,5-tetrahydro-2-oxo-1H-1-benzazepin-1-acetic acid | 20 mg |
| Corn starch | 60 mg |
| Lactose | 135 mg |
| Gelatine (as 10% solution) | 6 mg. |

The active substance, the corn starch and the lactose were thickened with the 10% gelatine solution. The paste was comminuted and the resulting granules were placed on a suitable sheet and dried at 45° C. The dried granules were fed through a crushing machine and mixed with the following further adjuvants in a mixer:

| | |
|---|---:|
| Talc | 5 mg |
| Magnesium stearate | 5 mg |
| Corn starch | 9 mg |
| and then compressed to form tablets of 240 mg. | |

EXAMPLE 2

Injection Solution Containing (3S,2'R)-3-[1-(2'-carboxy-4'-phenyl-butyl]-cyclopentan-1-carbonylamino]-2,3,4,5-tetrahydro-2-oxo-1 H-1-benzazepin-1-acetic acid An injection solution having the following composition per 5 ml was prepared:

| | |
|---|---:|
| (3S,2'R)-3-[1-(2'-carboxy-4'-phenyl-butyl)-cyclopentan-1-carbonylamino]-2,3,4,5-tetrahydro-2-oxo-1H-1-benzazepin-1-acetic acid | 10 mg |
| Na$_2$HPO$_4$.7H$_2$O | 43.24 mg |
| Na$_2$HPO$_4$.2H$_2$O | 7.72 mg |
| NaCl | 30.0 mg |
| Purified water | 4,948.0 mg |

The solids were dissolved in water, the solution was sterilized and was poured into ampoules in portions of 5 ml each.

EXAMPLE 3

Preferred compounds of Formula I for use according to the invention for the preparation of medicaments for the prophylaxis and/or treatment of damage to the heart which is caused by oxidative-toxic and in particular cardiotoxic doses of medicaments, in particular for adjuvant treatment in therapies with such medicaments, such as in cytostatic chemotherapy, include, for example, the following compounds or pharmaceutically acceptable salts thereof:

3-(1-[2'-(ethoxycarbonyl)-4'-phenyl-butyl]-cyclopentan-1-carbonylamino]-2,3,4,5-tetrahydro-2-oxo-1 H-1-benzazepin-1-acetic acid tert. butyl ester.

3-(1-[2'-(ethoxycarbonyl)-4'-phenyl-butyl]-cyclopentan-1-carbonylamino]-2,3,4,5-tetrahydro-2-oxo-1 H-1-benzazepin-1-acetic acid.

(3S,2'R)-3-{1-[2'-ethoxycarbonyl)-4'-phenyl-butyl]-cyclopentan-1 -carbonylamino}-2,3,4,5-tetrahydro-2-oxo-1 H-1-benzazepin-1-acetic acid tert. butyl ester.

(3S,2'R)-3-{1-[2'-(ethoxycarbonyl)-4'-phenyl-butyl]-cyclopentan-1 -carbonylamino}-2,3,4,5-tetrahydro-2-oxo-1 H-1-benzazepin-1-acetic acid.

3-{1-[2'-(tert.-butoxycarbonyl)-4'-phenyl-butyl]-cyclopentan-1-carbonylamino}-2,3,4,5-tetrahydro-2-oxo-1 H-1-benzazepin-1-acetic acid tert. butyl ester.

3-[1-(2'-carboxy-4'-phenyl-butyl)-cyclopentan-1-carbonylamino]-2,3,4,5-tetrahydro-2-oxo-1H-1-benzazepin-1-acetic acid.

3-{1-[2'-(tert. butoxycarbonyl)-4'-phenyl-butyl]-cyclopentan-1-carbonylamino}-2,3,4,5-tetrahydro-2-oxo-1 H-1-benzazepin-1-acetic acid benzyl ester.

3-[1-(2'-carboxy-4'-phenyl-butyl)-cyclopentan-1-carbonylamino]-2,3,4,5-tetrahydro-2-oxo-1 H-1-benzazepin-1-acetic acid benzyl ester.

3-{1-[2'-(tert. butylcarbonyloxymethoxycarbonyl)-4'-phenyl-butyl]-cyclopentan-1-carbonylamino}-2,3,4,5-tetrahydro-2-oxo-1 H-1-benzazepin-1-acetic acid benzyl ester.

3-{1-[2'-(pivaloyloxymethoxycarbonyl)-4'-phenyl-butyl]-cyclopentan-1-carbonylamino}-2,3,4,5-tetrahydro-2-oxo-1 H-1-benzazepin-1-acetic acid.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A method of inhibiting or treating heart damage induced by a cardiotoxic medicament in a mammal, said method comprising administering to said mammal an effective cardioprotective amount of a compound corresponding to Formula I

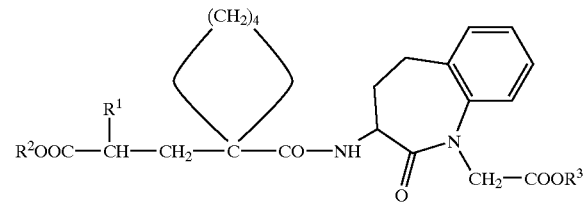

wherein
$R^1$ is a phenyl lower-alkyl group which may optionally be substituted in the phenyl ring by lower alkyl, lower alkoxy or halogen, or for a naphthyl lower-alkyl group,
$R^2$ is hydrogen or a group forming a biolabile ester, and
$R^3$ is hydrogen or a group forming a biolabile ester,
or a physiologically compatible salt thereof.

2. A method according to claim 1, wherein said medicament is a cytostatic agent.

3. A method according to claim 2, wherein said cytostatic agent is a cytostatic antibiotic.

4. A method according to claim 1, wherein said mammal is a human.

5. A method according to claim 1, wherein said mammal has suffered myocardial damage.

6. A method according to claim 1, wherein at least one of $R^2$ and $R^3$ is a group forming a biolabile ester.

7. A method according to claim 6, wherein the group which forms a biolabile ester is a lower alkyl group, or a phenyl or phenyl lower-alkyl group which is optionally substituted in the phenyl ring by lower alkyl or by a lower alkylene chain bonded to 2 adjacent carbon atoms.

8. A method according to claim 7, wherein the compound is (3S,2'R)-3-{1-[2'-(ethoxycarbonyl)-4'-phenyl-butyl]-cyclopentane-1-carbonylamino}-2,3,4,5-tetrahydro-2-oxo-1H-1-benzazepin-1-acetic acid or a physiologically compatible salt thereof.

9. A method according to claim 7, wherein the group which forms a biolabile ester is a phenyl, benzyl or indanyl group or a dioxolanylmethyl group, optionally substituted in the dioxolane ring by lower alkyl.

10. A method according to claim 9, wherein the group which forms a biolabile ester is a (2,2-dimethyl-1,3-dioxolan-4-yl)methyl group or a $C_2$–$C_6$-alkanoyloxymethyl group, optionally substituted at the oxymethyl group by lower alkyl.

11. A method according to claim 1, wherein $R^2$ is a group forming a biolabile ester and $R^3$ is hydrogen.

12. In the therapeutic administration to a mammal of a substance having oxidative-cytotoxic side effects, the improvement comprising administering to said mammal an effective oxidative-cytotoxic side effect inhibiting amount of a compound corresponding to Formula I

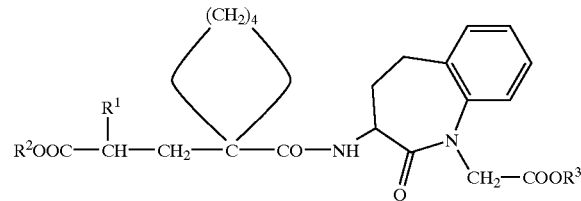

wherein
$R^1$ is a phenyl lower-alkyl group which may optionally be substituted in the phenyl ring by lower alkyl, lower alkoxy or halogen, or for a naphthyl lower-alkyl group,
$R^2$ is hydrogen or a group forming a biolabile ester, and
$R^3$ is hydrogen or a group forming a biolabile ester,
or a physiologically compatible salt thereof.

13. The improvement of claim 12, wherein said mammal is a human.

14. The improvement of claim 12, wherein said compound inhibits oxidative-cardiotoxic, side-effects.

15. The improvement of claim 12, wherein said compound or physiologically compatible salt thereof is co-administered simultaneously with said substance.

16. The improvement according to claim 12, wherein at least one of $R^2$ and $R^3$ is a group forming a biolabile ester.

17. The improvement according to claim 12, wherein the group which forms a biolabile ester is a lower alkyl group, or a phenyl or phenyl lower-alkyl group which is optionally substituted in the phenyl ring by lower alkyl or by a lower alkylene chain bonded to 2 adjacent carbon atoms.

18. The improvement according to claim 17, wherein the compound is (3S,2'R)-3-{1-[2'-(ethoxycarbonyl)-4'-phenyl-butyl]-cyclopentane-1 -carbonylamino}-2,3,4,5-tetrahydro-2-oxo-1 H-1-benzazepin-1-acetic acid or a physiologically compatible salt thereof.

19. The improvement according to claim 17, wherein the group which forms a biolabile ester is a phenyl, benzyl or indanyl group or a dioxolanylmethyl group, optionally substituted in the dioxolane ring by lower alkyl.

20. The improvement according to claim 19, wherein the group which forms a biolabile ester is a (2,2-dimethyl-1,3-dioxolan-4-yl)methyl group or a $C_2$–$C_6$-alkanoyl-oxymethyl group, optionally substituted at the oxymethyl group by lower alkyl.

21. The improvement according to claim 12, wherein $R^2$ is a group forming a biolabile ester and $R^3$ is hydrogen.

22. The improvement according to claim 12, wherein said substance is selected from the group consisting of the anthracyclines, mitoxantrone and prodrugs thereof.

23. A pharmaceutical composition according to claim 22, wherein said medicament is an anthracycline selected from the group consisting of daunorubicin, doxorubicin (adriamycin), epirubicin, and prodrugs thereof.

24. A pharmaceutical composition comprising in combination a medicament having cardiotoxic, oxidative-cytotoxic or oxidative-cardiotoxic side-effects, and a compound corresponding to Formula I

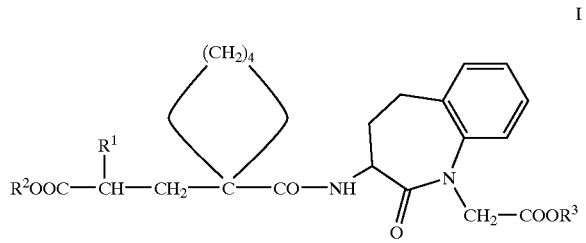

wherein
$R^1$ is a phenyl lower-alkyl group which may optionally be substituted in the phenyl ring by lower alkyl, lower alkoxy or halogen, or for a naphthyl lower-alkyl group,
$R^2$ is hydrogen or a group forming a biolabile ester, and
$R^3$ is hydrogen or a group forming a biolabile ester,
or a physiologically compatible salt thereof.

25. A pharmaceutical composition according to claim 24, wherein said medicament is a cytostatic agent having cardiotoxic side-effects.

26. A pharmaceutical composition according to claim 24, wherein said medicament is a cytostatic antibiotic.

27. A pharmaceutical composition according to claim 24, wherein said medicament is selected from the group consisting of the anthracyclines, mitoxantrone and prodrugs thereof.

28. A pharmaceutical composition according to claim 27, wherein said medicament is an anthracycline selected from the group consisting of daunorubicin, doxorubicin (adriamycin), epirubicin, and prodrugs thereof.

29. A pharmaceutical composition according to claim 24, wherein at least one of $R^2$ and $R^3$ in said compound is a group forming a biolabile ester.

30. A pharmaceutical composition according to claim 29, wherein the group which forms a biolabile ester is a lower alkyl group, or a phenyl or phenyl lower-alkyl group which is optionally substituted in the phenyl ring by lower alkyl or by a lower alkylene chain bonded to 2 adjacent carbon atoms.

31. A pharmaceutical composition according to claim 29, wherein the compound is (3S,2'R)-3-{1-[2'-(ethoxycarbonyl)-4'-phenyl-butyl]-cyclopentane-1-carbonylamino}-2,3,4,5-tetrahydro-2-oxo-1 H-1-benzazepin-1-acetic acid or a physiologically compatible salt thereof.

32. A pharmaceutical composition according to claim 29, wherein the group which forms a biolabile ester is a phenyl, benzyl or indanyl group or a dioxolanylmethyl group, optionally substituted in the dioxolane ring by lower alkyl.

33. A pharmaceutical composition according to claim 32, wherein the group which forms a biolabile ester is a (2,2-dimethyl-1,3-dioxolan-4-yl)methyl group or a $C_2$–$C_6$-alkanoyloxymethyl group, optionally substituted at the oxymethyl group by lower alkyl.

34. A pharmaceutical composition according to claim 24, wherein $R^2$ in said compound is a group forming a biolabile ester and $R^3$ is hydrogen.

* * * * *